United States Patent [19]
Dunnington et al.

[11] Patent Number: 5,840,536
[45] Date of Patent: Nov. 24, 1998

[54] GROWTH FACTOR RECEPTOR-BINDING INSULIN RECEPTOR

[76] Inventors: Damien J. Dunnington; James D. Frantz; Steven E. Shoelson, all of SmithKline Beecham Corporation, Corporate Intellectual Property—UW2220, P.O. Box 1539, King of Prussia, Pa. 19406-0939

[21] Appl. No.: 890,094

[22] Filed: Jul. 9, 1997

Related U.S. Application Data

[60] Provisional application No. 60/022,703 Jul. 9, 1996.

[51] Int. Cl.$^6$ ................................................... C12N 15/00
[52] U.S. Cl. ...................... 435/69.1; 536/23.5; 536/23.1; 530/350
[58] Field of Search ............................... 435/69.1, 320.1, 435/335, 252.3; 536/23.5, 23.1; 530/350

[56] References Cited

U.S. PATENT DOCUMENTS 5,434,064  7/1995  Schlessinger et al. ................ 435/172.3

OTHER PUBLICATIONS

Frantz et al., J.Biol.Chem. 272 (5):2659–67, Jan. 31, 1997.
O'Neill et al., J.Biol.Chem 271(37):22506–13, Sep. 13, 1996.
Nagase et al., DNA Research 3:321–9, 1996.
Levitzki et al., "Tyrosine Kinase Inhibition: An Approach to Drug Development" *Science*, vol. 267, pp. 1782–1788 (1995).
G. Shaw, "The Pleckstrin Homology Domain: An Intriguing Multifunctional Protein Module" *Bioessays*, vol. 18, pp. 35–46 (1996).
F. Liu and R. A. Roth, "Grb–IR: A SH2–Domain–Containing Protein that Binds to the Insulin Receptor and Inhibits its Function" *Proc. Natl. Acad. Sci. USA*, vol. 92, pp. 10287–10291 (1995).

F. Tamanoi, "Inhibitors of Ras Farnesyltransferases" *Trends in Biochemical Sciences*, vol. 18, pp. 349–353 (1993).
Paterson et al. "Phospholipase C $\delta_1$ Requires a Pleckstrin Homology Domain for Interaction with a Plasma Membrane" *Biochem. J.*, vol. 312, pp. 661–666 (1995).
D. Wang and G. Shaw, "The Association of the C–terminal Region of $\beta\Sigma$II Spectrin to Brain Membranes is Mediated by a PH Domain, does not Require Membrane Proteins, and Coincides with a Inositol–1,4,5 Trisphosphate Binding Site" *Biochem. Biophys. Res. Commun.*, vol. 217, pp. 608–615 (1995).
Garcia et al., "The Pleckstrin Homology Domain of Phospholipase C–$\delta_1$ Binds with High Affinity to Phosphatidylinositol 4,5–Biophosphate in Bilayer Membranes" *Biochemistry*, vol. 34, pp. 16228–16234 (1995).
Margolis et al., "High–Efficiency Expression/Cloning of Epidermal Growth Factor–Receptor–Binding Proteins with Src Homology 2 Domains" *Proc. Natl. Acad. Sci. USA*, vol. 89, pp. 8894–8898 (1992).
Auffray et al., "IMAGE: intégration au niveau moleculaire de l'analyse du genome humain et de son expression", *C.R. Acad. Sci.*, vol. 318, pp. 263–272 (1995).
J. Ooi, "The Cloning of Grb10 Reveals a New Family of SH2 Domain Proteins", *Oncogene*, vol. 10, pp. 1621–1630 (1995).

*Primary Examiner*—Stephen Walsh
*Assistant Examiner*—Eliane Lazar-Wesley
*Attorney, Agent, or Firm*—Kirk Baumeister; Charles M. Kinzig

[57] ABSTRACT

Isolated nucleic acid encoding a growth factor receptor binding protein-insulin receptor isoform, protein obtainable from the nucleic acid, recombinant host cells transformed with the nucleic acid and use of the protein and nucleic acid sequence are disclosed.

12 Claims, 3 Drawing Sheets

```
              1                                                                   50
GrbIR-1   ..........  ..........  ..........  ..........  ..........
Grb-IR    MALAGCPDSF  LHHPYYQDKV  EQTPRSQQDP  AGPGLPAQSD  RLANHQEDDV
mGrb10    ..........  ..........  ..........  ..........  ..........
hGrb7     ..........  ..........  ..........  ..........  ..........

51                                                                  100
GrbIR-1   ........MN  ASLESLYSAC  SMQS..DTVP  LLQNGQHARS  QPRASGPPRS
Grb-IR    DLEALVNDMN  ASLESLYSAC  SMQS..DTVP  LLQNGQHARS  QPRASGPPRS
mGrb10    ....MNNDIN  SSVESLNSAC  NMQSDTDTAP  LLEDGQHASN  QGAASSSR..
hGrb7     ..........  ..MELDLSPP  HLSSSPEDL.  .........W  PAPGTPPGTP 101                                                                 150
GrbIR-1   IQPQVSPRQR  VQRSQPVHI.  LAVRRLQEED  QQFRTSSLPA  IPNPFPELCG
Grb-IR    IQPQVSPRQR  VQRSQPVHI.  LAVRRLQEED  QQFRTSSLPA  IPNPFPELCG
mGrb10    GQPQASPRQK  MQRSQPVHI.  L..RRLQEED  QQLRTASLPA  IPNPFPELTG
hGrb7     RPPDTPLPEE  VKRSQPLLIP  TTGRKLREEE  R..RATSLPS  IPNPFPELCS 151                                                                 200
GrbIR-1   ..PGSPPVLT  PGSL..PPSQ  AAAKQ.....  ..........  ..........
Grb-IR    ..PGSPPVLT  PGSL..PPSQ  AAAKQ.....  ..........  ..........
mGrb10    AAPGSPPSVA  PSSLPPPPSQ  PPAKHCGRCE  KWIPGENTRG  NGKRKIWRWQ
hGrb7     PPSQSPILGG  PSSARGLLPR  DASRPHV...  ..........  ..........

201                                                                 250
GrbIR-1   ..........  ..........  ..........  ..........  ..........
Grb-IR    ..........  ..........  ..........  ..........  ..........
mGrb10    FPPGFQLSKL  TRPGLWTKTT  ARFSKKQPKN  QCPTDTVNPV  ARMPTSQMEK
hGrb7     ..........  ..........  ..........  ..........  ..........

251                                                                 300
GrbIR-1   .....DVKVF  SEDGTSKVVE  ILADMTARDL  CQLLVYKSHC  VDDNSWTLVE
Grb-IR    .....DVKVF  SEDGTSKVVE  ILADMTARDL  CQLLVYKSHC  VDDNSWTLVE
mGrb10    LRLRKDVKVF  SEDGTSKVVE  ILTDMTARDL  CQLLVYKSHC  VDDNSWTLVE
hGrb7     ......VKVY  SEDGACRSVE  VAAGATARHV  CEMLVQRAHA  LSDETWGLVE 301                                                   350
GrbIR-1   HHPHLGLERC  LEDHELVVQV  EST..MASES  KFLFRKNYAK  YEFFK.NPMN
Grb-IR    HHPHLGLERC  LEDHELVVQV  EST..MASES  KFLFRKNYAK  YEFFK.NPMN
mGrb10    HHPQLGLERC  LEDHEIVVQV  EST..MPSES  KFLFRKNYAK  YEFFK.NPVN
hGrb7     CHPHLALERG  LEDHESVVEV  QAAWPVGGDS  RFVFRKNFAK  YELFKSSPHS 351                                                                 400
GrbIR-1   FFPEQMVTWC  QQSNG..SQT  QLLQNFLNSS  SCPEIQGFLH  VKELGKKSWK
Grb-IR    FFPEQMVTWC  QQSNG..SQT  QLLQ......  ..........  ..........
mGrb10    FFPDQMVNWC  QQSNG..GQA  QLLQNFLNTS  SCPEIQGFLQ  VKEVGRKSWK
hGrb7     LFPEKMVSSC  LDAHTGISHE  DLIQNFLNAG  SFPEIQGFLQ  LRGSGRKLWK 401                                                                 450
GrbIR-1   KLYVCLRRSG  LYCSTKGTSK  EPRHLQLLAD  LEDSNIFSLI  AGRKQYNAPT
Grb-IR    ..........  ..........  EPRHLQLLAD  LEDSNIFSLI  AGRKQYNAPT
mGrb10    KLYVCLRRSG  LYYSTKGTSK  EPRHLQLLAD  LEESSIFYLI  AGKKQYNAPN
hGrb7     RFFCFLRRSG  LYYSTKGTSK  DPRHLQYVAD  VNESNVYVVT  QGRKLYGMPT 451                                                                 500
GrbIR-1   DHGLCIKPNK  VRNETKELRL  LCAEDEQTRT  CWMTAFRLLK  YEMLLYQNYR
Grb-IR    DHGLCIKPNK  VRNETKELRL  LCAEDEQTRT  CWMTAFRLLK  YGMLLYQNYR
mGrb10    EHGMCIKPNK  AKTEMKELRL  LCAEDEQIRT  CWMTAFRLLK  YGMLLYQNYR
hGrb7     DFGFCVKPNK  LRNGHKGLRI  FCSEDEQSRT  CWLAAFRLFK  YGVQLYKNYQ
```

FIGURE 1A/2

```
              501                                                       550
GrbIR-1    IPQQRKALLS  PF.STPVRSV  SENSLVAMDF  SGQTGRVIEN  PAEAQSAALE
Grb-IR     IPQQRKALLS  PF.STPVRSV  SENSLVAMDF  SGQTGRVIEN  PAEAQSAALE
mGrb10     IP.QRKGLPP  PF.NAPMRSV  SENSLVAMDF  SGQIGRVIDN  PAEAQSAALE
hGrb7      QAQSRHLHPS  CLGSPPLRSA  SDNTLVAMDF  SGHAGRVIEN  PREALSVALE 551                                                       600
GrbIR-1    EGHAWRKRST  RMNILGSQSP  LHPSTLSTVI  HRTQHWFHGR  FSREESHRII
Grb-IR     EGHAWRKRST  RMNILGSQSP  LHPSTLSTVI  HRTQHWFHGR  ISREESHRII
mGrb10     EGHAWRNGST  RMNILSSQSP  LHPSTLNAVI  HRTQHWFHGR  ISREESHRII
hGrb7      EAQAWRKKTN  HR..LSLPMP  ASGTSLSAAI  HRTQLWFHGR  ISREESQRLI 601                                                       650
GrbIR-1    KQQGLVDGLF  LLRDSQSNPK  AFVLTLCHHQ  KIKNFQILPC  EDDGQTFFSL
Grb-IR     KQQGLVDGLF  LLRDSQSNPK  AFVLTLCHHQ  KIKNFQILPC  EDDGQTFFSL
mGrb10     KQQGLVDGLF  LLRDSQSNPK  AFVLTLCHHQ  KIKNFQILPC  EDDGQTFFTL
hGrb7      GQQGLVDGLF  LVRESQRNPQ  GFVLSLCHLQ  KVKHYLILPS  EEEGRLYFSM 651                           687
GrbIR-1    DDGNTKFSDL  IQLVDFYQLN  KGVLPCKLKH  HCIRVAL
Grb-IR     DDGNTKFSDL  IQLVDFYQLN  KGVLPCKLKH  HCIRVAL
mGrb10     DDGNTKFSDL  IQLVDFYQLN  KGVLPCKLKH  HCIRVAL
hGrb7      DDGQTRFTDL  LQLVEFHQLN  RGILPCLLRH  CCTRVAL
```

FIGURE 1B/2

```
  1 ........MNASLESLYSACSMQSDTVPLLQNGQHARSQPRASGPPRSIQ  42
            ||||||||||||||||||||||||||||||||||||||||||
 51 DLEALVNDMNASLESLYSACSMQSDTVPLLQNGQHARSQPRASGPPRSIQ 100

43 PQVSPRQRVQRSQPVHILAVRRLQEEDQQFRTSSLPAIPNPFPELCGPGS  92
    ||||||||||||||||||||||||||||||||||||||||||||||||||
101 PQVSPRQRVQRSQPVHILAVRRLQEEDQQFRTSSLPAIPNPFPELCGPGS 150

93 PPVLTPGSLPPSQAAAKQDVKVFSEDGTSKVVEILADMTARDLCQLLVYK 142
    ||||||||||||||||||||||||||||||||||||||||||||||||||
151 PPVLTPGSLPPSQAAAKQDVKVFSEDGTSKVVEILADMTARDLCQLLVYK 200

143 SHCVDDNSWTLVEHHPHLGLERCLEDHELVVQVESTMASESKFLFRKNYA 192
    ||||||||||||||||||||||||||||||||||||||||||||||||||
201 SHCVDDNSWTLVEHHPHLGLERCLEDHELVVQVESTMASESKFLFRKNYA 250

193 KYEFFKNPMNFFPEQMVTWCQQSNGSQTQLLQNFLNSSSCPEIQGFLHVK 242
    |||||||||||||||||||||||||||||||
251 KYEFFKNPMNFFPEQMVTWCQQSNGSQTQLLQ................. 282

243 ELGKKSWKKLYVCLRRSGLYCSTKGTSKEPRHLQLLADLEDSNIFSLIAG 292
                                ||||||||||||||||||||||
283 .......................EPRHLQLLADLEDSNIFSLIAG 304

293 RKQYNAPTDHGLCIKPNKVRNETKELRLLCAEDEQTRTCWMTAFRLLKYE 342
    |||||||||||||||||||||||||||||||||||||||||||||||:
305 RKQYNAPTDHGLCIKPNKVRNETKELRLLCAEDEQTRTCWMTAFRLLKYG 354

343 MLLYQNYRIPQQRKALLSPFSTPVRSVSENSLVAMDFSGQTGRVIENPAE 392
    ||||||||||||||||||||||||||||||||||||||||||||||||||
355 MLLYQNYRIPQQRKALLSPFSTPVRSVSENSLVAMDFSGQTGRVIENPAE 404

393 AQSAALEEGHAWRKRSTRMNILGSQSPLHPSTLSTVIHRTQHWFHGRFSR 442
    ||||||||||||||||||||||||||||||||||||||||||||||:||
405 AQSAALEEGHAWRKRSTRMNILGSQSPLHPSTLSTVIHRTQHWFHGRISR 454

443 EESHRIIKQQGLVDGLFLLRDSQSNPKAFVLTLCHHQKIKNFQILPCEDD 492
    ||||||||||||||||||||||||||||||||||||||||||||||||||
455 EESHRIIKQQGLVDGLFLLRDSQSNPKAFVLTLCHHQKIKNFQILPCEDD 504

493 GQTFFSLDDGNTKFSDLIQLVDFYQLNKGVLPCKLKHHCIRVAL 536
    |||||||||||||||||||||||||||||||||||||||||||
505 GQTFFSLDDGNTKFSDLIQLVDFYQLNKGVLPCKLKHHCIRVAL 548
```

FIGURE 2/2

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 2505 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (v) FRAGMENT TYPE:

(vi) ORIGINAL SOURCE:

(xi) SEQUENCE DESCRIPTION: SEQ ID NO:1:

| | | | | | | |
|---|---|---|---|---|---|---|
| CGGCGCAACT | TTGGCTCCCA | GGGAACAAAC | ATCCTCCTTC | TAAGTGGTAG | ATGTGGGTGA | 60 |
| GCTGACCCTG | CTGGAGTCTG | TCCCCTGGGC | TACCCTCTGC | TTCCCCCCAT | TGTGAGTGGT | 120 |
| CCGTGAAGCA | CAGCGTTGAC | CAGACCTAAG | CCTGTTTGCT | CCCAGGACAA | GGTGGAGCAG | 180 |
| ACACCTCGCA | GTCAACAAGA | CCCGGCAGGA | CCAGGACTCC | CCGCACAGTC | TGACCGACTT | 240 |
| GCGAATCACC | AGGAGGATGA | TGTGGACCTG | GAAGCCCTGG | TGAACGATAT | GAATGCATCC | 300 |
| CTGGAGAGCC | TGTACTCGGC | CTGCAGCATG | CAGTCAGACA | CGGTGCCCCT | CCTGCAGAAT | 360 |
| GGCCAGCATG | CCCGCAGCCA | GCCTCGGGCT | TCAGGCCCTC | CTCGGTCCAT | CCAGCCACAG | 420 |
| GTGTCCCCGA | GGCAGAGGGT | GCAGCGCTCC | CAGCCTGTGC | ACATCCTCGC | TGTCAGGCGC | 480 |
| CTTCAGGAGG | AAGACCAGCA | GTTTAGAACC | TCATCTCTGC | CGGCCATCCC | CAATCCTTTT | 540 |
| CCTGAACTCT | GTGGCCCTGG | GAGCCCCCCT | GTGCTCACGC | CGGGTTCTTT | ACCTCCGAGC | 600 |
| CAGGCCGCCG | CAAAGCAGGA | TGTTAAAGTC | TTTAGTGAAG | ATGGGACAAG | CAAAGTGGTG | 660 |
| GAGATTCTAG | CAGACATGAC | AGCCAGAGAC | CTGTGCCAAT | TGCTGGTTTA | CAAAAGTCAC | 720 |
| TGTGTGGATG | ACAACAGCTG | GACACTAGTG | GAGCACCACC | CGCACCTAGG | ATTAGAGAGG | 780 |
| TGCTTGGAAG | ACCATGAGCT | GGTGGTCCAG | GTGGAGAGTA | CCATGGCCAG | TGAGAGTAAA | 840 |
| TTTCTATTCA | GGAAGAATTA | CGCAAAATAC | GAGTTCTTTA | AAAATCCCAT | GAATTTCTTC | 900 |
| CCAGAACAGA | TGGTTACTTG | GTGCCAGCAG | TCAAATGGCA | GTCAAACCCA | GCTTTTGCAG | 960 |
| AATTTTCTGA | ACTCCAGTAG | TTGTCCTGAA | ATTCAAGGGT | TTTTGCATGT | GAAAGAGCTG | 1020 |
| GGAAAGAAAT | CATGGAAAAA | GCTGTATGTG | TGTTTGCGGA | GATCTGGCCT | TTATTGCTCC | 1080 |
| ACCAAGGGAA | CTTCAAAGGA | ACCCAGACAC | CTGCAGCTGC | TGGCCGACCT | GGAGGACAGC | 1140 |
| AACATCTTCT | CCCTGATCGC | TGGCAGGAAG | CAGTACAACG | CCCCTACAGA | CCACGGGCTC | 1200 |
| TGCATAAAGC | CAAACAAAGT | CAGGAATGAA | ACTAAAGAGC | TGAGGTTGCT | CTGTGCAGAG | 1260 |
| GACGAGCAAA | CCAGGACGTG | CTGGATGACA | GCGTTCAGAC | TCCTCAAGTA | TGAAATGCTC | 1320 |
| CTTTACCAGA | ATTACCGAAT | CCCTCAGCAG | AGGAAGGCCT | TGCTGTCCCC | GTTCTCGACG | 1380 |
| CCAGTGCGCA | GTGTCTCCGA | GAACTCCCTC | GTGGCAATGG | ATTTTCTGG | GCAAACAGGA | 1440 |
| CGCGTGATAG | AGAATCCGGC | GGAGGCCCAG | AGCGCAGCCC | TGGAGGAGGG | CCACGCCTGG | 1500 |
| AGGAAGCGAA | GCACACGGAT | GAACATCCTA | GGTAGCCAAA | GTCCCCTCCA | CCCTTCTACC | 1560 |
| CTAAGTACAG | TGATTCACAG | GACACAGCAC | TGGTTTCACG | GGAGGTTCTC | CAGGGAGGAA | 1620 |
| TCCCACAGGA | TCATTAAACA | GCAAGGGCTC | GTGGATGGGC | TTTTTCTCCT | CCGTGACAGC | 1680 |
| CAGAGTAATC | CAAAGGCATT | TGTACTCACA | CTGTGTCATC | ACCAGAAAAT | TAAAAATTTC | 1740 |
| CAGATCTTAC | CTTGCGAGGA | CGACGGGCAG | ACGTTCTTCA | GCCTAGATGA | CGGGAACACC | 1800 |
| AAATTCTCTG | ACCTGATCCA | GCTGGTTGAC | TTTTACCAGC | TGAACAAAGG | AGTCCTGCCT | 1860 |
| TGCAAACTCA | AGCACCACTG | CATCCGAGTG | GCCTTATGAC | CGCAGATGTC | CTCTCGGCTG | 1920 |
| AAGACTGGAG | GAAGTGAACA | CTGGAGTGAA | GAAGCGGTCT | GTGCGTTGGT | GAAGAACACA | 1980 |
| CATCGATTCT | GCACCTGGGG | ACCCAGAGCG | AGATGGGTTT | GTTCGGTGCC | AGCCTACCAA | 2040 |
| GATTGACTAG | TTTGTTGGAC | TTAAACGACG | ATTTGCTGCT | GTGAACCCAG | CAGGGTCGCC | 2100 |
| TCCCTCTGCG | TCGGNCAAAT | TGGGGAGGGC | ATGGAAGATC | CAGCGGAAAG | TTGAAAATAA | 2160 |
| ACTGGAATGA | TCATCTTGGC | TTGGGCCGCT | TAGGAACAAG | AACCGGAGAG | AAGTGATTGG | 2220 |

```
AAATGAACTC  TTGCCCTGGA  ATAATCTTGA  CAATTAAAAC  TGATATGTTT  ACTTTTTTTG      2280

TATTGATCAC  TTTTTGGAC   TCCTTCTTTG  TTTTCAATAT  TGTATTCAGC  CTATTGTAGG      2340

AGGGGGATGT  GGCGTTTCAA  CTCATATAAT  ACAGAAAGAG  TTTTGGAATG  GGCAGATTTC      2400

AAACTGAATA  TGGGTCCCCA  AATGTTCCCA  GAGGGTCCTC  CACAACCTCT  GNCGACTACC      2460

ACGGTGTNGG  ATTCAGCTCC  CAAATGACAA  ACCCAGNCCT  TCCCA                       2505
```

( 2 ) INFORMATION FOR SEQ ID NO:2:

( i ) SEQUENCE CHARACTERISTICS:
        ( A ) LENGTH: 536 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met  Asn  Ala  Ser  Leu  Glu  Ser  Leu  Tyr  Ser  Ala  Cys  Ser  Met  Gln  Ser
 1              5                      10                      15

Asp  Thr  Val  Pro  Leu  Leu  Gln  Asn  Gly  Gln  His  Ala  Arg  Ser  Gln  Pro
              20                      25                      30

Arg  Ala  Ser  Gly  Pro  Pro  Arg  Ser  Ile  Gln  Pro  Gln  Val  Ser  Pro  Arg
              35                      40                      45

Gln  Arg  Val  Gln  Arg  Ser  Gln  Pro  Val  His  Ile  Leu  Ala  Val  Arg  Arg
         50                      55                      60

Leu  Gln  Glu  Glu  Asp  Gln  Gln  Phe  Arg  Thr  Ser  Ser  Leu  Pro  Ala  Ile
65                      70                      75                      80

Pro  Asn  Pro  Phe  Pro  Glu  Leu  Cys  Gly  Pro  Gly  Ser  Pro  Pro  Val  Leu
                   85                      90                      95

Thr  Pro  Gly  Ser  Leu  Pro  Pro  Ser  Gln  Ala  Ala  Ala  Lys  Gln  Asp  Val
              100                     105                     110

Lys  Val  Phe  Ser  Glu  Asp  Gly  Thr  Ser  Lys  Val  Val  Glu  Ile  Leu  Ala
              115                     120                     125

Asp  Met  Thr  Ala  Arg  Asp  Leu  Cys  Gln  Leu  Leu  Val  Tyr  Lys  Ser  His
         130                     135                     140

Cys  Val  Asp  Asp  Asn  Ser  Trp  Thr  Leu  Val  Glu  His  His  Pro  His  Leu
145                     150                     155                     160

Gly  Leu  Glu  Arg  Cys  Leu  Glu  Asp  His  Glu  Leu  Val  Val  Gln  Val  Glu
                   165                     170                     175

Ser  Thr  Met  Ala  Ser  Glu  Ser  Lys  Phe  Leu  Phe  Arg  Lys  Asn  Tyr  Ala
              180                     185                     190

Lys  Tyr  Glu  Phe  Phe  Lys  Asn  Pro  Met  Asn  Phe  Phe  Pro  Glu  Gln  Met
              195                     200                     205

Val  Thr  Trp  Cys  Gln  Gln  Ser  Asn  Gly  Ser  Gln  Thr  Gln  Leu  Leu  Gln
         210                     215                     220

Asn  Phe  Leu  Asn  Ser  Ser  Ser  Cys  Pro  Glu  Ile  Gln  Gly  Phe  Leu  His
225                     230                     235                     240

Val  Lys  Glu  Leu  Gly  Lys  Lys  Ser  Trp  Lys  Lys  Leu  Tyr  Val  Cys  Leu
                   245                     250                     255
```

| | | | | | | | | | | | | | | | |
|---|---|---|---|---|---|---|---|---|---|---|---|---|---|---|---|
|Arg|Arg|Ser|Gly 260|Leu|Tyr|Cys|Ser|Thr 265|Lys|Gly|Thr|Ser|Lys 270|Glu|Pro|
|Arg|His|Leu 275|Gln|Leu|Leu|Ala|Asp 280|Leu|Glu|Asp|Ser|Asn 285|Ile|Phe|Ser|
|Leu|Ile|Ala 290|Gly|Arg|Lys|Gln 295|Tyr|Asn|Ala|Pro|Thr 300|Asp|His|Gly|Leu|
|Cys 305|Ile|Lys|Pro|Asn|Lys 310|Val|Arg|Asn|Glu|Thr 315|Lys|Glu|Leu|Arg|Leu 320|
|Leu|Cys|Ala|Glu|Asp 325|Glu|Gln|Thr|Arg|Thr 330|Cys|Trp|Met|Thr|Ala 335|Phe|
|Arg|Leu|Leu|Lys 340|Tyr|Glu|Met|Leu|Leu 345|Tyr|Gln|Asn|Tyr|Arg 350|Ile|Pro|
|Gln|Gln|Arg|Lys 355|Ala|Leu|Leu|Ser|Pro 360|Phe|Ser|Thr|Pro|Val 365|Arg|Ser|
|Val|Ser|Glu 370|Asn|Ser|Leu|Val 375|Ala|Met|Asp|Phe|Ser 380|Gly|Gln|Thr|Gly|
|Arg 385|Val|Ile|Glu|Asn|Pro 390|Ala|Glu|Ala|Gln|Ser 395|Ala|Ala|Leu|Glu|Glu 400|
|Gly|His|Ala|Trp|Arg 405|Lys|Arg|Ser|Thr|Arg 410|Met|Asn|Ile|Leu|Gly 415|Ser|
|Gln|Ser|Pro|Leu 420|His|Pro|Ser|Thr|Leu 425|Ser|Thr|Val|Ile|His 430|Arg|Thr|
|Gln|His|Trp 435|Phe|His|Gly|Arg|Phe 440|Ser|Arg|Glu|Glu|Ser 445|His|Arg|Ile|
|Ile|Lys 450|Gln|Gln|Gly|Leu|Val 455|Asp|Gly|Leu|Phe|Leu 460|Leu|Arg|Asp|Ser|
|Gln 465|Ser|Asn|Pro|Lys|Ala 470|Phe|Val|Leu|Thr|Leu 475|Cys|His|His|Gln|Lys 480|
|Ile|Lys|Asn|Phe|Gln 485|Ile|Leu|Pro|Cys|Glu 490|Asp|Asp|Gly|Gln|Thr 495|Phe|
|Phe|Ser|Leu|Asp 500|Asp|Gly|Asn|Thr|Lys 505|Phe|Ser|Asp|Leu|Ile 510|Gln|Leu|
|Val|Asp|Phe 515|Tyr|Gln|Leu|Asn|Lys 520|Gly|Val|Leu|Pro|Cys 525|Lys|Leu|Lys|
|His|His 530|Cys|Ile|Arg|Val|Ala 535|Leu| | | | | | | | |

( 2 ) INFORMATION FOR SEQ ID NO:3:

( i ) SEQUENCE CHARACTERISTICS:
        ( A ) LENGTH: 2420 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

| | | | | | | |
|---|---|---|---|---|---|---|
|AATAATTCTC|AAATTTTTCT|TACTTACCTA|AATATAAGCT|AATTTCTATA|ACTCTAATTC|60|
|CTCAAAAGGT|ACTCCCTCTC|TCTCTCTCTC|TCTCTCCCTC|TCTCCTAGCA|CCTGCTGCTC|120|
|AGTAGGAAGG|GCAAGAGCAA|TTCGAGGCCG|GTGCATTGTG|AGGAGTCTCC|ACCCCTCCTC|180|

-continued

| | | | | | | |
|---|---|---|---|---|---|---|
| CTGCGCTTCC | TTCTCCAGGG | AGCCTCTCAG | GCCGCCCTCA | CCTGCCCGAG | ATAATTTTAG | 240 |
| TTTCCCTGGG | CCTGGAATCT | GGATACGCAG | GGCCTCGCTC | TATATTCTCC | CGCCTCAACA | 300 |
| TTCCAAAGGC | GGGATAGCCT | TTCTACCATC | TGTAGAGAAG | AGAGAAAGGA | TTCGAAATCA | 360 |
| AATCCAAGTG | TCTGGGATCT | CTAGACAGAG | CCAGACTTTG | GGCCGGGTGT | CCGGCTCCTT | 420 |
| CTGTTGGAGG | TGCTCCAGGT | GCCATGGAAC | TGGATCTGAG | CCCGACTCAT | CTCAGCAGCT | 480 |
| CCCCAGAAGA | TGTGTGCCCA | ACTCCTGCTA | CCCCTCCTGA | GACTCCTCCG | CCCCCTGATA | 540 |
| ACCCTCCGCC | AGGGGATGTG | AAGCGGTCGC | AGCCTTTGCC | CATCCCCAGC | AGCAGGAAAC | 600 |
| TTCGAGAAGA | GGAGTTTCAG | GCAACCTCTC | TGCCCTCCAT | CCCCAACCCC | TTCCCTGAGC | 660 |
| TCTGCAGCCC | ACCTTCACAG | AAACCCATTC | TTGGTGGTTC | CTCCGGTGCA | AGGGGGTTGC | 720 |
| TTCCTCGAGA | CTCCAGCCGC | CTCTGTGTGG | TGAAGGTGTA | CAGTGAGGAT | GGGGCCTGCC | 780 |
| GGTCTGTGGA | GGTGGCAGCG | GGCGCCACAG | CTCGTCACGT | GTGTGAGATG | CTGGTACAAC | 840 |
| GAGCTCACGC | CCTGAGCGAC | GAGAGCTGGG | GACTAGTGGA | ATCCCACCCC | TACCTGGCAC | 900 |
| TGGAGCGGGG | TCTGGAGGAC | CATGAATTTG | TGGTGGAAGT | GCAGGAGGCC | TGGCCTGTGG | 960 |
| GTGGAGATAG | CCGCTTCATC | TTCCGTAAAA | ACTTCGCCAA | GTATGAACTA | TTCAAGAGCC | 1020 |
| CCCCACACAC | CCTGTTTCCA | GAAAAGATGG | TCTCGAGCTG | TCTGGATGCA | CAAACAGGCA | 1080 |
| TATCCCATGA | AGACCTCATC | CAGAACTTCC | TGAACGCTGG | CAGCTTCCCT | GAGATCCAGG | 1140 |
| GCTTCCTGCA | GCTGCGGGGA | TCAGGCCGGG | GGTCAGGTCG | AAAGCTTTGG | AAACGTTTCT | 1200 |
| TCTGCTTTCT | GCGTCGATCT | GGCCTCTACT | ACTCTACCAA | GGGTACCTCC | AAGGACCCCA | 1260 |
| GACACCTACA | GTATGTGGCA | GATGTGAATG | AGTCCAATGT | CTATGTGGTG | ACCCAGGGCC | 1320 |
| GCAAGCTGTA | TGGGATGCCC | ACTGACTTCG | GCTTCTGTGT | CAAGCCCAAC | AAGCTTCGAA | 1380 |
| ACGGCACAA | GGGGCTCCAC | ATCTTCTGCA | GTGAGGATGA | GCAGAGTCGG | ACCTGCTGGC | 1440 |
| TGGCTGCCTT | CCGGCTCTTC | AAGTACGGGG | TACAGCTATA | TAAGAATTAT | CAGCAGGCCC | 1500 |
| AGTCTCGTCA | CCTGCGCCTA | TCCTATTTGG | GGTCTCCACC | CTTGAGGAGC | GTCTCAGACA | 1560 |
| ATACCCTAGT | GGCTATGGAC | TTCTCTGGCC | ATGCGGGGCG | TGTCATTGAT | AACCCCCGGG | 1620 |
| AAGCTCTGAG | TGCCGCCATG | GAGGAGGCCC | AGGCCTGGAG | GAAGAAGACA | AACCACCGTC | 1680 |
| TGAGCCTGCC | CACCACATGC | TCTGGCTCGA | GCCTCAGCGC | AGCCATTCAT | CGCACCCAGC | 1740 |
| CCTGGTTTCA | TGGACGCATC | TCTCGGGAGG | AGAGCCAGCG | GCTAATTGGA | CAGCAGGGCC | 1800 |
| TGGTGGATGG | TGTGTTCCTG | GTCCGGGAGA | GCCAGAGGAA | CCCACAGGGC | TTTGTCCTGT | 1860 |
| CCTTGTGCCA | TCTGCAGAAA | GTCAAGCATT | ATCTCATTTT | GCCAAGTGAA | GATGAAGGTT | 1920 |
| GCCTTTACTT | CAGCATGGAT | GAGGGCCAGA | CCCGTTTCAC | AGACCTGCTG | CAGCTGGTAG | 1980 |
| AATTCCACCA | GCTGAACCGA | GGCATCCTGC | CCTGCCTGCT | GCGCCACTGC | TGTGCCCGTG | 2040 |
| TGGCCCTCTG | AGGCCGCACA | AGCTACTGCA | GCCATGGGTT | TGCCTACCAC | CCTTCTGTCC | 2100 |
| TGTGGACTCG | GTGCAGGTGG | GTGGGGTGGT | AAACAGTGGA | AGAGCTCCCC | CCCCCAATTT | 2160 |
| TATCCCATTT | TTTTTAACCT | CTCTCAACCA | GTGAAACATC | CCCTAACCCT | GTCCATCCCT | 2220 |
| GACTCCTGTC | CCCAAGGGAG | GCATTGTGGT | CCTGTCCCCT | TGGTAGAGCT | CCTGAGGTAC | 2280 |
| TGTTCCAGTG | AGGGGCATTA | TGAGAGGAGC | GGGGCAGCCC | AGGAGGTCTC | ATACCCCACC | 2340 |
| CATAATCTGT | ACAGACTGAG | AGGCCAGTTG | ATCTGCTCTG | TTTTATACCA | GTAACAATAA | 2400 |
| AGATTATTTT | TTGATACAAA | | | | | 2420 |

( 2 ) INFORMATION FOR SEQ ID NO:4:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

GATTGGTGGC GACGACTCC 19

( 2 ) INFORMATION FOR SEQ ID NO:5:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

CCCGTGAAAC CAGTGCTGTG 20

( 2 ) INFORMATION FOR SEQ ID NO:6:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

GTAATACGAC TCACTATAGG GC 22

( 2 ) INFORMATION FOR SEQ ID NO:7:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

GGTAGCCAAA GTCCCCTCCA 20

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

GATTGGTGGC GACGACTCC 19

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

TGGAGGGGAC TTTGGCTACC 20

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

GGAATTCCAT GAATGCATCC CTGGAGAG 28

( 2 ) INFORMATION FOR SEQ ID NO:11:

( i ) SEQUENCE CHARACTERISTICS:
 ( A ) LENGTH: 28 base pairs
 ( B ) TYPE: nucleic acid
 ( C ) STRANDEDNESS: single
 ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

CCCTCGAGTC ATAAGGCCAC TCGGATGC 28

( 2 ) INFORMATION FOR SEQ ID NO:12:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

GTGAGCTGAC CCTGCTGGAG 20

( 2 ) INFORMATION FOR SEQ ID NO:13:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

AGACCTAAGC CTGTTTGCTC C 21

( 2 ) INFORMATION FOR SEQ ID NO:14:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

ACCGTGTCTG ACTGCATGCT                                                                                        20

(2) INFORMATION FOR SEQ ID NO:15:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

TGAAGTTCCC TTGGTGGAGC                                                                                        20

(2) INFORMATION FOR SEQ ID NO:16:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

CCCGTGAAAC CAGTGCTGTG                                                                                        20

(2) INFORMATION FOR SEQ ID NO:17:

(i) SEQUENCE CHARACTERISTICS:
                (A) LENGTH: 2070 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

AAATGTAATT TGAAGAAGGC AGAAGGAACC CATGGCTTTA GCCGGCTGCC CAGATTCCTT            60

TTTGCACCAT CCGTACTACC AGGACAAGGT GGAGCAGACA CCTCGCAGTC AACAAGACCC          120

| | | | | | | |
|---|---|---|---|---|---|---|
| GGCAGGACCA | GGACTCCCCG | CACAGTCTGA | CCGACTTGCG | AATCACCAGG | AGGATGATGT | 180 |
| GGACCTGGAA | GCCCTGGTGA | ACGATATGAA | TGCATCCCTG | GAGAGCCTGT | ACTCGGCTG | 240 |
| CAGCATGCAG | TCAGACACGG | TGCCCCTCCT | GCAGAATGGC | CAGCATGCCC | GCAGCCAGCC | 300 |
| TCGGGCTTCA | GGCCCTCCTC | GGTCCATCCA | GCCACAGGTG | TCCCCGAGGC | AGAGGGTGCA | 360 |
| GCGCTCCCAG | CCTGTGCACA | TCCTCGCTGT | CAGGCGCCTT | CAGGAGGAAG | ACCAGCAGTT | 420 |
| TAGAACCTCA | TCTCTGCCGG | CCATCCCCAA | TCCTTTTCCT | GAACTCTGTG | GCCCTGGGAG | 480 |
| CCCCCCTGTG | CTCACGCCGG | GTTCTTACC | TCCGAGCCAG | GCCGCCGCAA | AGCAGGATGT | 540 |
| TAAAGTCTTT | AGTGAAGATG | GGACAAGCAA | AGTGGTGGAG | ATTCTAGCAG | ACATGACAGC | 600 |
| CAGAGACCTG | TGCCAATTGC | TGGTTTACAA | AAGTCACTGT | GTGGATGACA | ACAGCTGGAC | 660 |
| ACTAGTGGAG | CACCACCCGC | ACCTAGGATT | AGAGAGGTGC | TTGGAAGACC | ATGAGCTGGT | 720 |
| GGTCCAGGTG | GAGAGTACCA | TGGCCAGTGA | GAGTAAATTT | CTATTCAGGA | AGAATTACGC | 780 |
| AAAATACGAG | TTCTTTAAAA | ATCCCATGAA | TTTCTTCCCA | GAACAGATGG | TTACTTGGTG | 840 |
| CCAGCAGTCA | AATGGCAGTC | AAACCCAGCT | TTTGCAGGAA | CCCAGACACC | TGCAGCTGCT | 900 |
| GGCCGACCTG | GAGGACAGCA | ACATCTTCTC | CCTGATCGCT | GGCAGGAAGC | AGTACAACGC | 960 |
| CCCTACAGAC | CACGGGCTCT | GCATAAAGCC | AAACAAAGTC | AGGAATGAAA | CTAAAGAGCT | 1020 |
| GAGGTTGCTC | TGTGCAGAGG | ACGAGCAAAC | CAGGACGTGC | TGGATGACAG | CGTTCAGACT | 1080 |
| CCTCAAGTAT | GGAATGCTCC | TTTACCAGAA | TTACCGAATC | CCTCAGCAGA | GGAAGGCCTT | 1140 |
| GCTGTCCCCG | TTCTCGACGC | CAGTGCGCAG | TGTCTCCGAG | AACTCCCTCG | TGGCAATGGA | 1200 |
| TTTTTCTGGG | CAAACAGGAC | GCGTGATAGA | GAATCCGGCG | GAGGCCCAGA | GCGCAGCCCT | 1260 |
| GGAGGAGGGC | CACGCCTGGA | GGAAGCGAAG | CACACGGATG | AACATCCTAG | GTAGCCAAAG | 1320 |
| TCCCCTCCAC | CCTTCTACCC | TAAGTACAGT | GATTCACAGG | ACACAGCACT | GGTTTCACGG | 1380 |
| GAGGATCTCC | AGGGAGGAAT | CCCACAGGAT | CATTAAACAG | CAAGGGCTCG | TGGATGGGCT | 1440 |
| TTTTCTCCTC | CGTGACAGCC | AGAGTAATCC | AAAGGCATTT | GTACTCACAC | TGTGTCATCA | 1500 |
| CCAGAAAATT | AAAAATTTCC | AGATCTTACC | TTGCGAGGAC | GACGGGCAGA | CGTTCTTCAG | 1560 |
| CCTAGATGAC | GGGAACACCA | AATTCTCTGA | CCTGATCCAG | CTGGTTGACT | TTTACCAGCT | 1620 |
| GAACAAAGGA | GTCCTGCCTT | GCAAACTCAA | GCACCACTGC | ATCCGAGTGG | CCTTATGACC | 1680 |
| GCAGATGTCC | TCTCGGCTGA | AGACTGGAGG | AAGTGAACAC | TGGAGTGAAG | AAGCGGTCTG | 1740 |
| TGCGTTGGTG | AAGAACACAC | ATCGATTCTG | CACCTGGGGA | CCCAGAGCGA | GATGGGTTTG | 1800 |
| TTCGGTGCCA | GCCGACCAAG | ATTGACTAGT | TTGTTGGACT | TAAACGACGA | TTTGCTGCTG | 1860 |
| TGAACCCAGC | AGGGTCGCCT | CCCTCTGCGT | CGGCCAAATT | GGGGAGGGCA | TGGAAGATCC | 1920 |
| AGCGGAAAGT | TGAAAATAAA | CTGGAATGAT | CATCTTGGCT | TGGGCCGCTT | AGGAACAAGA | 1980 |
| ACCGGAGAGA | AGTGATTGGA | AATGAACTCT | TGCCCTGGAA | TAATCTTGAC | AATTAAAACT | 2040 |
| GATATGTTTA | AAAAAAAAAA | AAAAAAACT | | | | 2070 |

( 2 ) INFORMATION FOR SEQ ID NO:18:

( i ) SEQUENCE CHARACTERISTICS:
        ( A ) LENGTH: 548 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:18:

```
Met Ala Leu Ala Gly Cys Pro Asp Ser Phe Leu His His Pro Tyr Tyr
 1               5                  10                  15
Gln Asp Lys Val Glu Gln Thr Pro Arg Ser Gln Gln Asp Pro Ala Gly
            20                  25                  30
Pro Gly Leu Pro Ala Gln Ser Asp Arg Leu Ala Asn His Gln Glu Asp
             35                  40                  45
Asp Val Asp Leu Glu Ala Leu Val Asn Asp Met Asn Ala Ser Leu Glu
         50                  55                  60
Ser Leu Tyr Ser Ala Cys Ser Met Gln Ser Asp Thr Val Pro Leu Leu
 65              70                  75                      80
Gln Asn Gly Gln His Ala Arg Ser Gln Pro Arg Ala Ser Gly Pro Pro
                 85                  90                  95
Arg Ser Ile Gln Pro Gln Val Ser Pro Arg Gln Arg Val Gln Arg Ser
            100                 105                 110
Gln Pro Val His Ile Leu Ala Val Arg Arg Leu Gln Glu Glu Asp Gln
            115                 120                 125
Gln Phe Arg Thr Ser Ser Leu Pro Ala Ile Pro Asn Pro Phe Pro Glu
        130                 135                 140
Leu Cys Gly Pro Gly Ser Pro Pro Val Leu Thr Pro Gly Ser Leu Pro
145                 150                 155                 160
Pro Ser Gln Ala Ala Ala Lys Gln Asp Val Lys Val Phe Ser Glu Asp
                165                 170                 175
Gly Thr Ser Lys Val Val Glu Ile Leu Ala Asp Met Thr Ala Arg Asp
            180                 185                 190
Leu Cys Gln Leu Leu Val Tyr Lys Ser His Cys Val Asp Asp Asn Ser
        195                 200                 205
Trp Thr Leu Val Glu His His Pro His Leu Gly Leu Glu Arg Cys Leu
    210                 215                 220
Glu Asp His Glu Leu Val Val Gln Val Glu Ser Thr Met Ala Ser Glu
225                 230                 235                 240
Ser Lys Phe Leu Phe Arg Lys Asn Tyr Ala Lys Tyr Glu Phe Phe Lys
                245                 250                 255
Asn Pro Met Asn Phe Phe Pro Glu Gln Met Val Thr Trp Cys Gln Gln
            260                 265                 270
Ser Asn Gly Ser Gln Thr Gln Leu Leu Gln Glu Pro Arg His Leu Gln
        275                 280                 285
Leu Leu Ala Asp Leu Glu Asp Ser Asn Ile Phe Ser Leu Ile Ala Gly
    290                 295                 300
Arg Lys Gln Tyr Asn Ala Pro Thr Asp His Gly Leu Cys Ile Lys Pro
305                 310                 315                 320
Asn Lys Val Arg Asn Glu Thr Lys Glu Leu Arg Leu Leu Cys Ala Glu
                325                 330                 335
Asp Glu Gln Thr Arg Thr Cys Trp Met Thr Ala Phe Arg Leu Leu Lys
            340                 345                 350
Tyr Gly Met Leu Leu Tyr Gln Asn Tyr Arg Ile Pro Gln Gln Arg Lys
        355                 360                 365
Ala Leu Leu Ser Pro Phe Ser Thr Pro Val Arg Ser Val Ser Glu Asn
    370                 375                 380
```

-continued

| | | | | | | | | | | | | | | | |
|---|---|---|---|---|---|---|---|---|---|---|---|---|---|---|---|
| Ser 385 | Leu | Val | Ala | Met | Asp 390 | Phe | Ser | Gly | Gln | Thr 395 | Gly | Arg | Val | Ile | Glu 400 |
| Asn | Pro | Ala | Glu | Ala 405 | Gln | Ser | Ala | Ala | Leu 410 | Glu | Glu | Gly | His | Ala 415 | Trp |
| Arg | Lys | Arg | Ser 420 | Thr | Arg | Met | Asn | Ile 425 | Leu | Gly | Ser | Gln | Ser 430 | Pro | Leu |
| His | Pro | Ser 435 | Thr | Leu | Ser | Thr | Val 440 | Ile | His | Arg | Thr | Gln 445 | His | Trp | Phe |
| His | Gly 450 | Arg | Ile | Ser | Arg | Glu 455 | Glu | Ser | His | Arg | Ile 460 | Ile | Lys | Gln | Gln |
| Gly 465 | Leu | Val | Asp | Gly | Leu 470 | Phe | Leu | Leu | Arg | Asp 475 | Ser | Gln | Ser | Asn | Pro 480 |
| Lys | Ala | Phe | Val | Leu 485 | Thr | Leu | Cys | His | His 490 | Gln | Lys | Ile | Lys | Asn 495 | Phe |
| Gln | Ile | Leu | Pro 500 | Cys | Glu | Asp | Asp | Gly 505 | Gln | Thr | Phe | Phe | Ser 510 | Leu | Asp |
| Asp | Gly | Asn 515 | Thr | Lys | Phe | Ser | Asp 520 | Leu | Ile | Gln | Leu | Val 525 | Asp | Phe | Tyr |
| Gln | Leu 530 | Asn | Lys | Gly | Val | Leu 535 | Pro | Cys | Lys | Leu | Lys 540 | His | His | Cys | Ile |
| Arg 545 | Val | Ala | Leu | | | | | | | | | | | | |

GROWTH FACTOR RECEPTOR-BINDING INSULIN RECEPTOR

RELATED APPLICATION

This application claims the benefit of U.S. Provisional application Ser. No. 60/022,703, filed Jul. 9, 1996.

FIELD OF THE INVENTION

The present invention relates to an isolated isoform of human growth factor receptor-binding insulin receptor protein (GrbIR-1) gene; to essentially pure human GrbIR-1 protein; and to compositions and methods of producing and using human GrbIR-1 sequences and proteins.

BACKGROUND OF THE INVENTION

A number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein tyrosine kinases (PTK) and phosphatases. Tyrosine phosphorylation is a major mediator of signal transduction in multicellular organisms. Receptor-bound, membrane-bound and intracellular PTKs regulate cell proliferation, cell differentiation and signalling processes in immune system cells.

Aberrant PTK activity has been implicated or is suspected in a number of pathologies such as diabetes, atherosclerosis, psoriasis, septic shock, bone loss, anemia, many cancers and other proliferative diseases. Accordingly, tyrosine kinases and the signal transduction pathways which they are part of are potential targets for drug design. For a review, see Levitzki et al. in *Science* 267, 1782–1788 (1995).

Many of the proteins comprising signal transduction pathways are present at low levels and often have opposing activities. The properties of these signalling molecules allow the cell to control transduction by means of the subcellular location and juxtaposition of effectors as well as by balancing activation with repression such that a small change in one pathway can achieve a switching effect.

The formation of transducing complexes by juxtaposition of the signalling molecules through protein-protein interactions are mediated by specific docking domain sequence motifs. Src homology 2 (SH2) domains, which are conserved non-catalytic sequences of approximately 100 amino acids found in a variety of signalling molecules such as non-receptor PTKs and kinase target effector molecules and in oncogenic proteins, play a critical role. The SH2 domains are highly specific for short phosphotyrosine-containing peptide sequences found in autophosphorylated PTK receptors or intracellular tyrosine kinases. Src homology 3 (SH3) domains, conserved sequences of approximately 50 amino acids that mediate protein-protein interactions through sequence-specific binding to proline-rich motifs in target proteins, are also critically involved in signal transduction. Pleckstrin homology (PH) domains are also involved in signal transduction and control membrane association of signaling molecules. See G. Shaw, *Bioessays* 18, 35–46 (1996). At least 90 proteins having conserved SH2, SH3 or PH domains, and, in many cases, distinct catalytic domains, are now known.

One approach towards the pharmacological regulation of signal transduction pathways is to design ligands which selectively bind to a chosen PH domain and thus affect the interaction of membrane-associated inositol 1,4,5-trisphosphate with its PH domain-containing target molecule, thereby modulating signal transduction. Any selective modulators would provide a useful lead for drug development.

Growth factor receptor binding protein-Inuslin Receptor (Grb-IR) is a cytoplasmic signalling molecule containing an SH2 domain and a partial PH domain with a wide tissue and cell distribution. The molecule was first described by F. Liu and R. A. Roth in *Proc Natl. Acad. Sci. USA* 92, 10287–10291 (1995). Interaction of Grb-IR with growth factor receptors such as the insulin receptor (IR) is mediated by the SH2 domain, can be dependent upon receptor tyrosine autophosphorylation and involves a direct interaction between Grb-IR and the phosphorylated receptors.

Further, binding of Grb-IR to the insulin receptor has been shown to inhibit subsequent signalling events such as insulin-dependent tyrosine phosphorylation of a 60k GAP-associated protein, IRS-1 and insulin induced association of phosphatidyl inositol-3 kinase with IRS-1 (Liu and Roth, supra). Thus, Grb-IR inhibits insulin signalling through the IR. Membrane association of signalling molecules is important for bringing them in close proximity to other effectors. An example is ras which is farnesylated at the C-terminus and thereby located to the plasma membrane. The importance of such localization is shown by the inhibitory effect of farnesyl transferase inhibitors on ras-mediated signal transduction. See Tamanoi, F., *Trends in Biochemical Sciences* 18, 349–353 (1993).

In the case of grb-IR, a PH domain could serve a similar purpose, since PH domains are known to facilitate membrane association of proteins through binding to inositol 1,4,5-trisphosphate residues in cell membranes. See H. F. Paterson et al., *Biochem. J.* 312, 661–666 (1995). Phospholipase C delta 1 requires a pleckstrin homology domain for interaction with the plasma membrane. See D. S. Wang & G. Shaw, *Biochem. Biophys. Res. Commun.* 217, 608–615 (1995). The association of the C-terminal region of beta I sigma II spectrin to brain membranes is mediated by a PH domain, does not require membrane proteins, and coincides with a inositol-1,4,5 triphosphate binding site. See P. Garcia et al., *Biochemistry* 34, 16228–16234 (1995). The pleckstrin homology domain of phospholipase C-delta 1 binds with high affinity to phosphatidylinositol 4,5-bisphosphate in bilayer membranes). However, the known grb-IR sequence lacks an intact PH domain.

The involvement of Grb-IR in the signal transduction of the insulin receptor pathway necessitates the identification of other human Grb-IR homologs and isoforms, preferably those containing intact PH domains, and their cDNAs. A need also exists for compounds which modulate the activity of Grb-IR homologs and isoforms, for methods to identify such modulators and for reagents useful in such methods.

SUMMARY OF THE INVENTION

Accordingly, one aspect of the present invention is an isolated polynucleotide selected from the group consisting of:

(a) a polynucleotide encoding human GrbIR-1 having the nucleotide sequence as set forth in SEQ ID NO:1 from nucleotide 289 to 1897;

(b) a polynucleotide capable of hybridizing to the complement of a polynucleotide according to (a) under moderately stringent hybridization conditions and which encodes a functional human GrbIR-1; and (c) a degenerate polynucleotide according to (a) or (b).

Another aspect of the invention is a functional polypeptide encoded by the polynucleotides of the invention.

Another aspect of the invention is a method for preparing essentially pure human GrbIR-1 protein comprising culturing a recombinant host cell comprising a vector comprising a polynucleotide of the invention under conditions promoting expression of the protein and recovery thereof.

Another aspect of the invention is an antisense oligonucleotide comprising a sequence which is capable of binding to the polynucleotide of the invention.

Another aspect of the invention is a modulator of the polypeptides of the invention.

Another aspect of the invention is a method for assaying a medium for the presence of a substance that modulates GrbIR-1 activity by affecting the binding of GrbIR-1 to cellular binding partners comprising the steps of:

(a) providing a GrbIR-1 protein having the amino acid sequence of GrbIR-1 (SEQ ID NO:2) or a functional derivative thereof and a cellular binding partner or synthetic analog thereof;

(b) incubating with a test substance which is suspected of modulating GrbIR-1 activity under conditions which permit the formation of a GrbIR-1 protein/cellular binding partner complex;

(c) assaying for the presence of the complex, free GrbIR-1 protein or free cellular binding partner; and (d) comparing to a control to determine the effect of the substance.

Another aspect of the invention is a method for assaying for the presence of a substance that modulates GrbIR-1 activity by direct binding to GrbIR-1 protein comprising the steps of:

(a) providing a labelled GrbIR-1 protein having the amino acid sequence of GrbIR-1 (SEQ ID NO:2) or a functional derivative thereof (b) providing solid support-associated modulator candidates;

(c) incubating a mixture of the labelled GrbIR-1 protein with the support-associated modulator candidates under conditions which can permit the formation of a GrbIR-1 protein/modulator candidate complex;

(d) separating the solid support from free soluble labelled GrbIR-1 protein;

(e) assaying for the presence of solid support-associated labelled protein;

(f) isolating the solid support complexed with labelled GrbIR-1 protein; and (g) identifying the modulator candidate.

Another aspect of the invention is GrbIR-1 protein modulating compounds identified by the methods of the invention.

Another aspect of the invention is a method for the treatment of a patient having need to modulate GrbIR-1 activity comprising administering to the patient a therapeutically effective amount of the modulating compounds of the invention.

Another aspect of the invention is a method of treating conditions which are related to insufficient GrbIR-1 protein function which comprises:

(a) isolating cells from a patient deficient in GrbIR-1 protein function;

(b) altering the cells by transfecting the polynucleotide of claim 1 into the cells wherein a GrbIR-1 protein is expressed; and (c) introducing the cells back to the patient to alleviate the condition.

Another aspect of the invention is a method of treating conditions which are related to insufficient GrbIR-1 protein function which comprises administering the polynucleotide of claim 1 to a patient deficient in GrbIR-1 protein function wherein a GrbIR-1 protein is expressed and alleviates the condition.

Another aspect of the invention is a transgenic non-human animal capable of expressing in any cell thereof the DNA encoding the polypeptides of the invention.

BRIEF DESCRIPTION OF THE DRAWINGS

FIG. 1 is a multiple amino acid sequence alignment of GrbIR-1, Grb-IR, murine Grb10 and human Grb7.

FIG. 2 is an amino acid sequence alignment of human GrbIR-1 with human Grb-IR.

DETAILED DESCRIPTION OF THE INVENTION

As used herein, the term "GrbIR-1 gene" refers to DNA molecules comprising a nucleotide sequence that encodes an isoform of human growth factor receptor binding insulin receptor. The GrbIR-1 gene sequence is listed in SEQ ID NO:1. The coding region of the GrbIR-1 gene consists of nucleotides 289 to 1897 of SEQ ID NO:1. The deduced 536 amino acid sequence of the GrbIR-1 gene product GrbIR-1 is listed in SEQ ID NO:2.

As used herein, the term "functional fragments" when used to modify a specific gene or gene product means a less than full length portion of the gene or gene product which retains substantially all of the biological function associated with the full length gene or gene product to which it relates. To determine whether a fragment of a particular gene or gene product is a functional fragment, fragments are generated by well-known nucleolytic or proteolytic techniques or by the polymerase chain reaction and the fragments tested for the described biological function.

As used herein, an "antigen" refers to a molecule containing one or more epitopes that will stimulate a host's immune system to make a humoral and/or cellular antigen-specific response. The term is also used herein interchangeably with "immunogen."

As used herein, the term "epitope" refers to the site on an antigen or hapten to which a specific antibody molecule binds. The term is also used herein interchangeably with "antigenic determinant" or "antigenic determinant site."

As used herein, "monoclonal antibody" is understood to include antibodies derived from one species (e.g., murine, rabbit, goat, rat, human, etc.) as well as antibodies derived from two (or perhaps more) species (e.g., chimeric and humanized antibodies).

As used herein, a coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

As used herein, a "replicon" is any genetic element (e.g., plasmid, chromosome, virus) that functions as an autonomous unit of DNA replication in vivo; i.e., capable of replication under its own control.

As used herein, a "vector" is a replicon, such as a plasmid, phage, or cosmid, to which another DNA segment may be attached so as to bring about the replication of the attached segment.

As used herein, a "reference" gene refers to the wild type human GrbIR-1 gene sequence of the invention and is understood to include the various sequence polymorphisms that exist, wherein nucleotide substitutions in the gene sequence exist, but do not affect the essential function of the gene product.

As used herein, a "mutant" gene refers human GrbIR-1 sequences different from the reference gene wherein nucleotide substitutions and/or deletions and/or insertions result in perturbation of the essential function of the gene product.

As used herein, a DNA "coding sequence of" or a "nucleotide sequence encoding" a particular protein, is a DNA sequence which is transcribed and translated into a polypeptide when placed under the control of appropriate regulatory sequences.

As used herein, a "promoter sequence" is a DNA regulatory region capable of binding RNA polymerase in a cell and initiating transcription of a downstream (3' direction) coding sequence. For purposes of defining the present invention, the promoter sequence is bound at its 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein, DNA "control sequences" refers collectively to promoter sequences, ribosome binding sites, polyadenylation signals, transcription termination sequences, upstream regulatory domains, enhancers and the like, which collectively provide for the expression (i.e., the transcription and translation) of a coding sequence in a host cell.

As used herein, a control sequence "directs the expression" of a coding sequence in a cell when RNA polymerase will bind the promoter sequence and transcribe the coding sequence into mRNA, which is then translated into the polypeptide encoded by the coding sequence.

As used herein, a "host cell" is a cell which has been transformed or transfected, or is capable of transformation or transfection by an exogenous DNA sequence.

As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

As used herein, "transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.) or by infection, in which viruses are used to transfer DNA into cells.

As used herein, a "target cell" is a cell that is selectively transfected over other cell types (or cell lines).

As used herein, a "clone" is a population of cells derived from a single cell or common ancestor by mitosis. A "cell line" is a clone of a primary cell that is capable of stable growth in vitro for many generations.

As used herein, a "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, a "modulator" of a polypeptide is a substance which can affect the polypeptide function.

An aspect of the present invention is isolated polynucleotides encoding a human GrbIR-1 protein including substantially similar sequences and functional fragments. Isolated polynucleotide sequences are substantially similar if they are capable of hybridizing under moderately stringent conditions to SEQ ID NO:1 or they encode DNA sequences which are degenerate to SEQ ID NO:1 or are degenerate to those sequences capable of hybridizing under moderately stringent conditions to SEQ ID NO:1.

Moderately stringent conditions is a term understood by the skilled artisan and has been described in, for example, Sambrook et al. *Molecular Cloning: A Laboratory Manual*, 2nd edition, Vol. 1, pp. 101–104, Cold Spring Harbor Laboratory Press (1989). An exemplary hybridization protocol using moderately stringent conditions is as follows. Nitrocellulose filters are prehybridized at 65° C. in a solution containing 6× SSPE, 5× Denhardt's solution (10 g Ficoll, 10 g BSA and 10 g polyvinylpyrrolidone per liter solution), 0.05% SDS and 100 ug/ml tRNA. Hybridization probes are labeled, preferably radiolabelled (e.g., using the Bios TAG-IT® kit). Hybridization is then carried out for approximately 18 hours at 65° C. The filters are then washed twice in a solution of 2× SSC and 0.5% SDS at room temperature for 15 minutes. Subsequently, the filters are washed at 58° C., air-dried and exposed to X-ray film overnight at −70° C. with an intensifying screen.

Degenerate DNA sequences encode the same amino acid sequence as SEQ ID NO:2 or the proteins encoded by that sequence capable of hybridizing under moderately stringent conditions to SEQ ID NO:1, but have variation(s) in the nucleotide coding sequences because of the degeneracy of the genetic code. For example, the degenerate codons UUC and UUU both code for the amino acid phenylalanine, whereas the four codons GGX all code for glycine.

Alternatively, substantially similar sequences are defined as those sequences in which about 70%, preferably about 80% and most preferably about 90%, of the nucleotides or amino acids match over a defined length of the molecule. As used herein, substantially similar refers to the sequences having similar identity to the sequences of the instant invention. Thus nucleotide sequences that are substantially the same can be identified by hybridization or by sequence comparison. Protein sequences that are substantially the same can be identified by techniques such as proteolytic digestion, gel electrophoresis and/or microsequencing. Excluded from the definition of substantially similar sequences is Grb-IR.

Embodiments of the isolated polynucleotides of the invention include DNA, genomic DNA and RNA, preferably of human origin. A method for isolating a nucleic acid molecule encoding a GrbIR-1 protein is to probe a genomic or cDNA library with a natural or artificially designed probe using art recognized procedures. See, e.g., "Current Protocols in Molecular Biology", Ausubel et al. (eds.) Greene Publishing Association and John Wiley Interscience, New York, 1989,1992. The ordinarily skilled artisan will appreciate that SEQ ID NO:1 or fragments thereof comprising at least 15 contiguous nucleotides are particularly useful probes. It is also appreciated that such probes can be and are preferably labeled with an analytically detectable reagent to facilitate identification of the probe. Useful reagents include, but are not limited to, radioisotopes, fluorescent dyes or enzymes capable of catalyzing the formation of a detectable product. The probes would enable the ordinarily skilled artisan to isolate complementary copies of genomic DNA, cDNA or RNA polynucleotides encoding GrbIR-1 proteins from human, mammalian or other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another aspect of the invention is functional polypeptides encoded by the polynucleotides of the invention. An embodiment of a functional polypeptide of the invention is the human GrbIR-1 protein having the amino acid sequence set forth in SEQ ID NO:2.

Another aspect of the invention is a method for preparing essentially pure human GrbIR-1 protein. Yet another aspect is the human GrbIR-1 protein produced by the preparation method of the invention. This protein has the amino acid sequence listed in SEQ ID NO:2 and includes variants with a substantially similar amino acid sequence that have the same function. The proteins of this invention are preferably made by recombinant genetic engineering techniques by culturing a recombinant host cell containing a vector encoding the polynucleotides of the invention under conditions promoting the expression of the protein and recovery thereof.

The isolated polynucleotides, particularly the DNAs, can be introduced into expression vectors by operatively linking the DNA to the necessary expression control regions, e.g., regulatory regions, required for gene expression. The vectors can be introduced into an appropriate host cell such as a prokaryotic, e.g., bacterial, or eukaryotic, e.g., yeast or mammalian cell by methods well known in the art. See Ausubel et al., supra. The coding sequences for the desired proteins, having been prepared or isolated, can be cloned into any suitable vector or replicon. Numerous cloning vectors are known to those of skill in the art and the selection of an appropriate cloning vector is a matter of choice. Examples of recombinant DNA vectors for cloning and host cells which they can transform include, but are not limited to, the bacteriophage λ (*E. coli*), pBR322 (*E. coli*), pACYC177 (*E. coli*), pGEX4T-3 (*E. coli*), pKT230 (gram-negative bacteria), pGV1106 (gram-negative bacteria), pLAFR1 (gram-negative bacteria), pME290 (non-*E.coli* gram-negative bacteria), pHV14 (*E. coli* and *Bacillus subtlilis*), pBD9 (Bacillus), pIJ61 (Streptomyces), pUC6 (Streptomyces), YIp5 (Saccharomyces), a baculovirus insect cell system, a Drosophila insect system, YCp19 (Saccharomyces) and pSV2neo (mammalian cells). See generally, "DNA Cloning": Vols. I & II, Glover et al. ed. IRL Press Oxford (1985) (1987); and T. Maniatis et al. ("Molecular Cloning" Cold Spring Harbor Laboratory (1982).

The gene can be placed under the control of control elements such as a promoter, ribosome binding site (for bacterial expression) and, optionally, an operator, so that the DNA sequence encoding the desired protein is transcribed into RNA in the host cell transformed by a vector containing the expression construct. The coding sequence may or may not contain a signal peptide or leader sequence. The proteins of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437 and 4,338,397.

In addition to control sequences, it may be desirable to add regulatory sequences which allow for regulation of the expression of the protein sequences relative to the growth of the host cell. Regulatory sequences are known to those of skill in the art. Exemplary are those which cause the expression of a gene to be turned on or off in response to a chemical or physical stimulus, including the presence of a regulatory compound or to various temperature or metabolic conditions. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences, i.e., RNA polymerase which binds to the DNA molecule at the control sequences transcribes the coding sequence. Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogues of human GrbIR-1 protein. Mutants or analogues may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; "DNA Cloning," Vols. I and II, supra; and "Nucleic Acid Hybridization", supra.

Depending on the expression system and host selected, the proteins of the present invention are produced by growing host cells transformed by an expression vector described above under conditions whereby the protein of interest is expressed. Preferred mammalian cells include human embryonic kidney cells (293), monkey kidney cells, fibroblast (COS) cells, Chinese hamster ovary (CHO) cells, Drosophila or murine L-cells. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform E. coli and pooling and screening individual colonies using polyclonal serum or monoclonal antibodies to human GrbIR-1.

The proteins of the present invention may also be produced by chemical synthesis such as solid phase peptide synthesis on an automated peptide synthesizer, using known amino acid sequences or amino acid sequences derived from the DNA sequence of the genes of interest. Such methods are known to those skilled in the art.

The proteins of the present invention or their fragments comprising at least one epitope can be used to produce antibodies, both polyclonal and monoclonal, directed to epitopes corresponding to amino acid sequences disclosed herein. If polyclonal antibodies are desired, a selected mammal such as a mouse, rabbit, goat or horse is immunized with a protein of the present invention, or its fragment, or a mutant protein. Serum from the immunized animal is collected and treated according to known procedures. Serum polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion and also by other techniques such as direct transformation of B lymphocytes with oncogenic DNA or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); and U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties, i.e., for isotype, epitope, affinity, etc. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed as reagents in immunoassays, RIA, ELISA, and the like. The antibodies of the invention can be labeled with an analytically detectable reagent such as a radioisotope, fluorescent molecule or enzyme.

Chimeric antibodies, in which non-human variable regions are joined or fused to human constant regions (see, e.g., Liu et al., Proc. Natl Acad. Sci. USA, 84, 3439 (1987)), may also be used in assays or therapeutically. Preferably, a therapeutic monoclonal antibody would be "humanized" as described in Jones et al., Nature, 321, 522 (1986); Verhoeyen et al., Science, 239, 1534 (1988); Kabat et al., J. Immunol., 147, 1709 (1991); Queen et al., Proc. Natl Acad. Sci. USA, 86, 10029 (1989); Gorman et al., Proc. Natl Acad. Sci. USA, 88, 34181 (1991); and Hodgson et al., Bio/Technology, 9:, 421 (1991).

Another aspect of the present invention is modulators of the polypeptides of the invention. Functional modulation of GrbIR-1 by a substance includes partial to complete inhibition of function, identical function, as well as enhancement of function. Embodiments of modulators of the invention include peptides, oligonucleotides and small organic molecules including peptidomimetics.

Another aspect of the invention is antisense oligonucleotides comprising a sequence which is capable of binding to the polynucleotides of the invention. Synthetic oligonucleotides or related antisense chemical structural analogs can be designed to recognize, specifically bind to and prevent transcription of a target nucleic acid encoding GrbIR-1 protein by those of ordinary skill in the art. See generally, Cohen, J. S., Trends in Pharm. Sci., 10, 435(1989) and Weintraub, H. M., Scientific American, January (1990) at page 40.

Another aspect of the invention is a method for assaying a medium for the presence of a substance that modulates GrbIR-1 protein function by affecting the binding of GrbIR-1 protein to cellular binding partners. Examples of modulators include, but are not limited to peptides and small organic molecules including peptidomimetics. A GrbIR-1 protein is provided having the amino acid sequence of human GrbIR-1 (SEQ ID NO:2) or a functional derivative thereof together with a cellular binding partner or synthetic analog thereof. The mixture is incubated with a test substance which is suspected of modulating GrbIR-1 activity, under conditions which permit the formation of a GrbIR-1 gene product/cellular binding partner complex. An assay is performed for the presence of the complex, free GrbIR-1 protein or free cellular binding partner and the result compared to a control to determine the effect of the test substance.

Another aspect of the invention is a method for assaying for the presence of a substance that modulates GrbIR-1 activity by direct binding to GrbIR-1 protein. Examples of modulators include, but are not limited to, peptides and small organic molecules including peptidomimetics. Modulator candidates are synthesized on a solid support by techniques such as those disclosed in Lam et al., Nature 354, 82 (1991) or Burbaum et al., Proc. Natl. Acad. Sci. USA 92, 6027 (1995) to provide solid support-associated modulator candidates. A labelled GrbIR-1 protein is provided having the amino acid sequence of human GrbIR-1 (SEQ ID NO:2) or a functional derivative thereof. Exemplary labels include directly attached fluorescent or colored dyes, biotin, radioisotopes or epitope tags, which are detectable by a suitable antibody. A mixture of solid support-associated modulator candidates and labelled GrbIR-1 protein is incubated under conditions which can permit the formation of a GrbIR-1 protein/modulator candidate complex. The solid support is separated from free soluble labelled GrbIR-1 protein. An assay is performed for the presence of solid support-associated labelled protein. Solid supports complexed with labelled protein are isolated and the identity of the modulator candidate determined by techniques well known to those skilled in the art.

Modulation of GrbIR-1 function would be expected to be useful for treatment of diabetes. Inhibition of grbIR-1 could be effected through antagonism of the SH2 domain/ phosphorylated IR interaction or through inhibition of the binding of the PH domain to phosphatidylinositol 4,5-bisphosphate.

Further, GrbIR-1 could be used to isolate proteins which interact with it and this interaction could be a target for interference. Inhibitors of protein-protein interactions between GrbIR-1 and other factors could lead to the development of pharmaceutical agents for the modulation of GrbIR-1 activity.

Methods to assay for protein-protein interactions, such as that of a GrbIR-1 gene product/binding partner complex, and to isolate proteins interacting with GrbIR-1 are known to those skilled in the art. Use of the methods discussed below enable one of ordinary skill in the art to accomplish these aims without undue experimentation.

The yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, GrbIR-1 cDNA is fused to a Gal4 transcription factor DNA binding domain and expressed in yeast cells. cDNA library members obtained from cells of interest are fused to a transactivation domain of Gal4. cDNA clones which express proteins which can interact with GrbIR-1 will lead to reconstitution of Gal4 activity and transactivation of expression of a reporter gene such as Gal1-lacZ. Optionally, the host cells can be co-transfected with a protein tyrosine kinase to induce tyrosine phosphorylation of members of the cDNA library. Such phosphorylation is necessary for optimum interaction with the SH2 domain of GrbIR-1.

An alternative method is screening of λgt11, λZAP (Stratagene) or equivalent cDNA expression libraries with recombinant GrbIR-1. Recombinant GrbIR-1 protein or fragments thereof are fused to small peptide tags such as FLAG, HSV or GST. The peptide tags can possess convenient phosphorylation sites for a kinase such as heart muscle creatine kinase or they can be biotinylated. Recombinant GrbIR-1 can be phosphorylated with $^{32}[P]$ or used unlabeled and detected with streptavidin or antibodies against the tags. λgt11cDNA expression libraries are made from cells of interest and are incubated with the recombinant GrbIR-1, washed and cDNA clones isolated which interact with GrbIR-1. See, e.g., T. Maniatis et al, supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled GrbIR-1, preferably iodinated, and detection of bound GrbIR-1 by autoradiography. See Sims et al., *Science* 241, 585–589 (1988) and McMahan et al., *EMBO J.* 10, 2821–2832 (1991). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing GrbIR-1 bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA* 84, 3365 (1987) and Aruffo et al., *EMBO J.* 6, 3313 (1987). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228, 810–815 (1985).

Another alternative method is isolation of proteins interacting with GrbIR-1 directly from cells. Fusion proteins of GrbIR-1 with GST or small peptide tags are made and immobilized on beads. Biosynthetically labeled or unlabeled protein extracts from the cells of interest are prepared, incubated with the beads and washed with buffer. Proteins interacting with GrbIR-1 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant GrbIR-1 is incubated with labeled or unlabeled cell extracts and immunoprecipitated with anti-GrbIR-1 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled GrbIR-1 is used to select peptides from a peptide or phosphopeptide library which interact with GrbIR-1. Sequencing of the peptides leads to identification of consensus peptide sequences which might be found in interacting proteins.

GrbIR-1 binding partners identified by any of these methods or other methods which would be known to those of ordinary skill in the art as well as those putative binding partners discussed above can be used in the assay method of the invention. Assaying for the presence of GrbIR-1/binding partner complex are accomplished by, for example, the yeast two-hybrid system, ELISA or immunoassays using antibodies specific for the complex. In the presence of test substances which interrupt or inhibit formation of GrbIR-1/ binding partner interaction, a decreased amount of complex will be determined relative to a control lacking the test substance.

Assays for free GrbIR-1 or binding partner are accomplished by, for example, ELISA or immunoassay using specific antibodies or by incubation of radiolabeled GrbIR-1 with cells or cell membranes followed by centrifugation or filter separation steps. In the presence of test substances which interrupt or inhibit formation of GrbIR-1/binding partner interaction, an increased amount of free GrbIR-1 or free binding partner will be determined relative to a control lacking the test substance.

Another aspect of the invention is pharmaceutical compositions comprising an effective amount of a GrbIR-1 modulator of the invention and a pharmaceutically acceptable carrier. Pharmaceutical compositions of modulators of this invention for parenteral administration, i.e., subcutaneously, intramuscularly or intravenously or oral administration can be prepared.

The compositions for parenteral administration will commonly comprise a solution of the modulators of the invention or a cocktail thereof dissolved in an acceptable carrier, preferably an aqueous carrier. A variety of aqueous carriers may be employed, e.g., water, buffered water, 0.4% saline, 0.3% glycine and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the modulator of the invention in such pharmaceutical formulation can vary widely, i.e., from less than about 0.5%, usually at or at least about 1% to as much as 15 or 20% by weight and will be selected primarily based on fluid volumes, viscosities, etc. according to the particular mode of administration selected.

Thus, a pharmaceutical composition of the modulator of the invention for intramuscular injection could be prepared to contain 1 mL sterile buffered water, and 50 mg of a protein of the invention. Similarly, a pharmaceutical composition of the modulator of the invention for intravenous infusion could be made up to contain 250 ml of sterile Ringer's solution, and 150 mg of a modulator of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The physician will determine the dosage of the present therapeutic agents which will be most suitable and it will vary with the form of administration and the particular compound chosen, and furthermore, it will vary with the particular patient under treatment. Generally, the physician will wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 1 to 10 milligrams per day and higher although it may be administered in several different dosage units.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance to the disease.

Single or multiple administrations of the pharmaceutical compositions can be carried out with dose levels and pattern being selected by the treating physician. In any event, the pharmaceutical composition of the invention should provide a quantity of the modulators of the invention sufficient to effectively treat the patient.

Additionally, some diseases result from inherited defective genes. These genes can be detected by comparing the sequence of the defective gene with that of a normal one. Individuals carrying mutations in the GrbIR-1 gene may be detected at the DNA level by a variety of techniques. Nucleic acids used for diagnosis (genomic DNA, mRNA etc.) may be obtained from a patient's cells, such as from blood, urine, saliva or tissue biopsy, e.g., chorionic villi sampling or removal of amniotic fluid cells and autopsy material. The genomic DNA may be used directly for detection or may be amplified enzymatically by using PCR, ligase chain reaction (LCR), strand displacement amplification (SDA), etc. prior to analysis. See, e.g., Saiki et al., *Nature*, 324, 163–166 (1986), Bej, et al., *Crit. Rev. Biochem. Molec. Biol.*, 26, 301–334 (1991), Birkenmeyer et al., *J. Virol. Meth.*, 35, 117–126 (1991), Van Brunt, J., *Bio/Technology*, 8, 291–294 (1990)). RNA or cDNA may also be used for the same purpose. As an example, PCR primers complementary to the nucleic acid of the instant invention can be used to identify and analyze GrbIR-1 mutations. For example, deletions and insertions can be detected by a change in size of the amplified product in comparison to the normal GrbIR-1 genotype. Point mutations can be identified by hybridizing amplified DNA to rabiolabeled GrbIR-1 RNA of the invention or alternatively, radiolabelled GrbIR-1 antisense DNA sequences of the invention. Perfectly matched sequences can be distinguished from mismatched duplexes by RNase A digestion or by differences in melting temperatures (Tm). Such a diagnostic would be particularly useful for prenatal and even neonatal testing.

In addition, point mutations and other sequence differences between the reference gene and "mutant" genes can be identified by yet other well-known techniques, e.g., direct DNA sequencing, single-strand conformational polymorphism. See Orita et al., *Genomics*, 5, 874–879 (1989). For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags. Cloned DNA segments may also be used as probes to detect specific DNA segments. The sensitivity of this method is greatly enhanced when combined with PCR. The presence of nucleotide repeats may correlate to a causative change in GrbIR-1 activity or serve as marker for various polymorphisms.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures. See, e.g., Myers et al., *Science*, 230, 1242 (1985). In addition, sequence alterations, in particular small deletions, may be detected as changes in the migration pattern of DNA heteroduplexes in nondenaturing gel electrophoresis such as heteroduplex electrophoresis. See, e.g., Nagamine et al., *Am. J. Hum. Genet.*, 45, 337–339 (1989). Sequence changes at specific locations may also be revealed by nuclease protection assays, such as RNase and S1 protection or the chemical cleavage method as disclosed by Cotton et al. in *Proc. Natl. Acad. Sci. USA*, 85, 4397–4401 (1985).

Thus, the detection of a specific DNA sequence may be achieved by methods such as hybridization (e.g., heteroduplex electroporation, see, White et al., *Genomics*, 12, 301–306 (1992), RNAse protection (e.g., Myers et al., *Science*, 230, 1242 (1985)) chemical cleavage (e.g., Cotton et al., *Proc. Natl. Acad. Sci. USA*, 85, 4397–4401 (1985))), direct DNA sequencing, or the use of restriction enzymes (e.g., restriction fragment length polymorphisms (RFLP) in which variations in the number and size of restriction fragments can indicate insertions, deletions, presence of nucleotide repeats and any other mutation which creates or destroys an endonuclease restriction sequence). Southen blotting of genomic DNA may also be used to identify large (i.e., greater than 100 base pair) deletions and insertions.

In addition to conventional gel electrophoresis and DNA sequencing, mutations such as microdeletions, aneuploidies, translocations, inversions, can also be detected by in situ analysis. See, e.g., Keller et al., DNA Probes, 2nd Ed., Stockton Press, New York, N.Y., USA (1993). That is, DNA or RNA sequences in cells can be analyzed for mutations without isolation and/or immobilization onto a membrane. Fluorescence in situ hybridization (FISH) is presently the most commonly applied method and numerous reviews of FISH have appeared. See, e.g., Trachuck et al., *Science*, 250, 559–562 (1990), and Trask et al., *Trends, Genet.*, 7, 149–154 (1991). Hence, by using nucleic acids based on the structure of the GrbIR-1 genes, one can develop diagnostic tests for genetic mutations.

In addition, some diseases are a result of, or are characterized by, changes in gene expression which can be detected by changes in the mRNA. Alternatively, the GrbIR-1 gene can be used as a reference to identify individuals expressing an increased or decreased level of GrbIR-1 protein, e.g., by Northern blotting or in situ hybridization.

Defining appropriate hybridization conditions is within the skill of the art. See, e.g., "Current Protocols in Mol. Biol." Vol. I & II, Wiley Interscience. Ausbel et al. (eds.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioisotopes, fluorescent dyes or enzymes capable of catalyzing the formation of a detectable product. As a general rule, the more stringent the hybridization conditions the more closely related genes will be that are recovered.

The putative role of GrbIR-1 in signal transduction of the insulin receptor pathway establishes yet another aspect of the invention which is gene therapy. "Gene therapy" means gene supplementation where an additional reference copy of a gene of interest is inserted into a patient's cells. As a result, the protein encoded by the reference gene corrects the defect and permits the cells to function normally, thus alleviating disease symptoms. The reference copy would be a wild-type form of the GrbIR-1 gene or a gene encoding a protein or peptide which modulates the activity of the endogenous GrbIR-1.

Gene therapy of the present invention can occur in vivo or ex vivo. Ex vivo gene therapy requires the isolation and purification of patient cells, the introduction of a therapeutic gene and introduction of the genetically altered cells back into the patient. A replication-deficient virus such as a modified retrovirus can be used to introduce the therapeutic GrbIR-1 gene into such cells. For example, mouse Moloney leukemia virus (MMLV) is a well-known vector in clinical gene therapy trials. See, e.g., Boris-Lauerie et al., *Curr. Opin. Genet. Dev.*, 3, 102–109 (1993).

In contrast, in vivo gene therapy does not require isolation and purification of a patient's cells. The therapeutic gene is typically "packaged" for administration to a patient such as in liposomes or in a replication-deficient virus such as adenovirus as described by Berkner, K. L., in *Curr. Top. Microbiol. Immunol.*, 158, 39–66 (1992) or adeno-associated virus (AAV) vectors as described by Muzyczka, N., in *Curr. Top. Microbiol. Immunol.*, 158, 97–129 (1992) and U.S. Pat. No. 5,252,479. Another approach is administration of "naked DNA" in which the therapeutic gene is directly injected into the bloodstream or muscle tissue. Another approach is administration of "naked DNA" in which the therapeutic gene is introduced into the target tissue by microparticle bombardment using gold particles coated with the DNA.

Cell types useful for gene therapy of the present invention include lymphocytes, hepatocytes, myoblasts, fibroblasts, any cell of the eye such as retinal cells, epithelial and endothelial cells. Preferably the cells are T lymphocytes drawn from the patient to be treated, hepatocytes, any cell of the eye or respiratory or pulmonary epithelial cells. Transfection of pulmonary epithelial cells can occur via inhalation of a neubulized preparation of DNA vectors in liposomes, DNA-protein complexes or replication-deficient adenoviruses. See, e.g., U.S. Pat. No. 5,240,846.

Another aspect of the invention is transgenic, non-human mammals capable of expressing the polynucleotides of the invention in any cell. Transgenic, non-human animals may be obtained by transfecting appropriate fertilized eggs or embryos of a host with the polynucleotides of the invention or with mutant forms found in human diseases. See, e.g., U.S. Pat. Nos. 4,736,866; 5,175,385; 5,175,384 and 5,175,386. The resultant transgenic animal may be used as a model for the study of GrbIR-1 gene function or for producing large amounts of grb-IR-1 protein for screening or crystallography purposes. Particularly useful transgenic animals are those which display a detectable phenotype associated with the expression of the GrbIR-1 protein. Drug development candidates may then be screened for their ability to reverse or exacerbate the relevant phenotype.

The present invention will now be described with reference to the following specific, non-limiting examples.

EXAMPLE 1

GrbIR-1 full-length cDNA Cloning and Sequence Analysis

A search of a random cDNA sequence database consisting of short partial sequences known as expressed sequence tags (ESTs) with SH2 domain encoding sequences using the BLASTX algorithm disclosed an EST which was homologous to a murine epidermal growth factor receptor-binding protein grb7 cDNA sequence reported by Margolis, B. L. et al. in *Proc. Natl. Acad. Sci. USA* 89, 8894–8898 (1992) (SEQ ID NO: 3). The EST was originally isolated from a human cerebellum cDNA library.

A 5'-rapid amplification of cDNA ends (5' RACE) protocol was used to isolate the 5' cDNA end of the putative human gene. Candidate 5' RACE products were amplified by PCR from a λgt11 human skeletal muscle library (Clontech cat no. HL1124b). The PCR contained 100 ng of phage DNA, a lambda-specific primer 5'GATTGGTGGC-GACGACTCC3' (SEQ ID NO: 4) and a gene-specific primer 5'CCCGTGAAACCAGTGCTGTG3' (SEQ ID NO: 5). Thirty cycles were conducted as follows: 94° C. for 20 s, 70° C. to 55° C. in 0.5° C. increments/cycle for 30 s and 72° C. for 2 min. A PCR product of 1.7 kb was purified and subcloned into pBluescript II and sequenced. Sequence analysis revealed the fragment to be the 5' end of the gene, containing the remaining coding sequence, including the N-terminus.

A cDNA encoding an intact coding sequence was assembled. A 3.4 kb PCR product was amplified from the EST using the primers T7 5'GTAATACGACTCACTATAGGGC3' (SEQ ID NO: 6) and 5'GGTAGCCAAAGTCCCCTCCA3' (SEQ ID NO: 7), and a 1.7 kb PCR product was amplified from the 5' RACE fragment isolated above using the primers 5'GATTGGTGGCGACGACTCC3' (SEQ ID NO: 8) and 5'TGGAGGGGACTTTGGCTACC3' (SEQ ID NO: 9). The PCR conditions were 94° C. for 15 s, 55° C. for 20 s, 72° C. for 4 min., for 25 cycles. These products were combined by PCR in a second reaction containing each of the above PCR products and the primers 5'GGAATTCCATGAATGCATCCCTGGAGAG3' (SEQ ID NO: 10) and 5'CCCTCGAGTCATAAGGCCACTCGGATGC3' (SEQ ID NO: 11). The PCR conditions were 94° C. for 15 s, 45° C. for 20 s, 72° C. for 2 min., for 25 cycles. The 1.6 kb secondary PCR product was treated with EcoRI and XhoI and subcloned into pGEX4T-3 (Pharmacia). The protein is expressed in E. coli strain LE392 at moderate levels upon IPTG induction and is soluble.

Independent confirmation of the existence of a mRNA corresponding to the full-length cDNA produced was carried out by RT-PCR. cDNA was prepared from 100 ng of human skeletal muscle polyA RNA (Clontech cat. no. 6541-1) using random hexamer primers and MoMLV reverse transcriptase. One twentieth of the cDNA was used as template in a PCR reaction containing the following primers sets: A1/P1, A2/P1, A2/P2, and A2/7-2 (A1: 5'GTGAGCTGACCCTGCTGGAG3' (SEQ ID NO: 12); A2: 5'AGACCTAAGCCTGTTTGCTCC3' (SEQ ID NO: 13); P1: 5'ACCGTGTCTGACTGCATGCT3' (SEQ ID NO: 14); P2: 5'TGAAGTTCCCTTGGTGGAGC3' (SEQ ID NO: 15); 7-2: 5'CCCGTGAAACCAGTGCTGTG3' (SEQ ID NO: 16)). The expected 288 bp, 203 bp, 954 bp and 1461 bp PCR fragments were observed, respectively. The PCR conditions were 94° C. for 15 s, 70° C. to 50° C. in 0.5 ûC increment/cycle for 20 s, 72° C. for 2 min., for 40 cycles. Control reactions containing either no template or the 1.6 kb recombined cDNA produced above gave either no PCR product or the expected fragments.

Sequence analysis of the full-length cDNA revealed a 1608 nucleotide open reading frame (SEQ ID NO: 1) encoding a 536 amino acid protein (SEQ ID NO: 2) with a predicted molecular mass of 59 kDa, starting with an ATG at position 289 and terminating with a TGA at position 1897 of SEQ ID NO: 1.

GenBank searches using the BLASTX and BLASTP algorithms with the full-length cDNA sequence or with the deduced amino acid sequence were carried out to identify homologous entries. The search results indicated that the isolated full-length cDNA is an alternatively spliced isoform of Grb-IR (Liu et al., supra, GenBank Accession U34355 (SEQ ID NO: 17 and SEQ ID NO: 18)) designated as GrbIR-1, and is a member of the Grb10/Grb7 family of SH2 adapter proteins. See FIG. 1 for a multiple sequence alignment of GrbIR-1, Grb-IR, murine Grb10 and human Grb7.

An alignment of Grb-IR and GrbIR-1 using the GAP algorithm is shown in FIG. 2 (top, GrbIR-1; bottom, GrbIR). The overall amino acid identity was 99.6% with one gap. GrbIR-1 contains an insert which restores an incomplete pleckstrin homology (PH) domain in Grb-IR and GrbIR-1 contains a shortened N-terminus when compared with Grb-IR. The regions other than the C-terminal SH2 domain and the PH domain did not show significant homologies to other database entries.

EXAMPLE 2

Tissue Distribution of GrbIR-1

Northern blots of tissue mRNA were conducted to determine the tissue distribution of grbIR-1 gene transcription. The CDNA insert was amplified by PCR using the primers T3 and T7 and the 3.5 kb product was purified. Twenty-five ng of the PCR product was radiolabelled with [32P]-dATP using random hexamer primers and used to probe human multiple tissue Northern blots (Clontech cat. nos. 7760-1 and 7759-1). The membranes were washed at high stringency and exposed for 6 hrs to a storage phosphor screen (Molecular Dynamics) for visualization. Expression of the corresponding mRNA was largely ubiquitous and variable in level in heart, brain, placenta, lung, liver, skeletal muscle, kidney, pancreas, spleen, thymus, prostate, testes, ovaries, small intestine and colon, although absent from peripheral blood leukocytes. The mRNA is approximately 5.6 kb in length. Highest expression was observed in heart, brain, skeletal muscle, and pancreas. Two additional transcripts are observed in skeletal muscle, of 4.8 and 3.1 kb. These may correspond to additional protein isoforms in this tissue.

The present invention may be embodied in other specific forms without departing from the spirit or essential attributes thereof, and, accordingly, reference should be made to the appended claims, rather than to the foregoing specification, as indicating the scope of the invention.

---

We claim:

1. An isolated polynucleotide selected from the group consisting of:
   (a) a polynucleotide encoding human GrbIR-1 having the nucleotide sequence as set forth in SEQ ID NO:1 from nucleotide 289 to 1897; and
   (b) a polynucleotide capable of hybridizing to the complement of a polynucleotide according to (a) under moderately stringent hybridization conditions and which encodes a functional human GrbIR-1 which binds to the insulin receptor and contains a pleckstrin homology domain as set forth in SEQ ID NO:2.

2. An isolated polynucleotide having the nucleotide sequence as set forth in SEQ ID NO:1.

3. An isolated polypeptide encoded by the polynucleotide of claim 1.

4. The polypeptide of claim 3 which is human GrbIR-1 having the amino acid sequence set forth in SEQ ID NO:2.

5. The polynucleotide of claim 1 which is DNA.

6. The polynucleotide of claim 5 which is genomic DNA.

7. The polynucleotide of claim 1 which is RNA.

8. A vector comprising the DNA of claim 5.

9. A recombinant host cell comprising the vector of claim 8.

10. A method for preparing essentially pure human GrbIR-1 protein comprising culturing the recombinant host cell of claim 9 under conditions promoting expression of the protein and recovering the expressed protein.

11. Human GrbIR-1 produced by the process of claim 10.

12. An isolated polynucleotide encoding the amino acid sequence of human GrbIR-1 as set forth in SEQ ID NO:2.

* * * * *